United States Patent [19]

Lu et al.

[11] Patent Number: 5,684,177
[45] Date of Patent: Nov. 4, 1997

[54] MISOPROSTOL

[75] Inventors: Yee-Fung Lu; Raymond So, both of Scarborough; Dan To, Richmond Hill; Casimir G. Antczak, Aurora, all of Canada

[73] Assignee: Torcan Chemical Ltd., Aurora, Canada

[21] Appl. No.: 649,402

[22] Filed: May 17, 1996

[51] Int. Cl.$^6$ .................................................. C07C 177/00
[52] U.S. Cl. ........................... 560/121; 556/112; 562/503
[58] Field of Search ........................... 560/121; 556/112; 562/503; 568/907; 585/375

[56] References Cited

U.S. PATENT DOCUMENTS 4,777,275  10/1988  Campbell et al. .................. 556/112
4,904,820   2/1990  Campbell et al. .................. 560/121

FOREIGN PATENT DOCUMENTS 1040197  10/1978  Canada ............................. 260/235.01

*Primary Examiner*—Joseph McKane
*Attorney, Agent, or Firm*—Ridout & Maybee

[57] ABSTRACT

In a process for making synthetic prostaglandin-type compounds such as misoprostol, organo metallic cuprate complexes capable of reacting with cyclopentenones are prepared by reaction of an alkyl lithium compound with a cuprous halide, followed by reaction of the resulting complex with a vinyl stannane, using an excess of alkyl lithium in the initial reaction and maintaining the excess present during the formation of the organo metallic cuprate complex.

10 Claims, No Drawings

MISOPROSTOL

FIELD OF THE INVENTION

This invention relates to organometallic synthetic processes and organometallic compounds useful therein. More specifically, it relates to methods of making organo-copper compounds which are useful in preparation of pharmaceutically active synthetic prostaglandin-type compounds.

BACKGROUND OF THE INVENTION AND PRIOR ART

Canadian Patent 1,040,197 Pappo et. al. describes 16-oxygenated prostanoic acid derivatives and processes for their preparation. At least one of the compounds described in this patent, namely (11α,13E)-(±)-11,16-dihydroxy-16-methyl-9-oxoprost-13-en-1-oic acid, methyl ester, the generic name of which is misoprostol, has gained significant pharmaceutical and commercial acceptance as an inhibitor of gastric acid secretion. It has the following structural chemical formula:

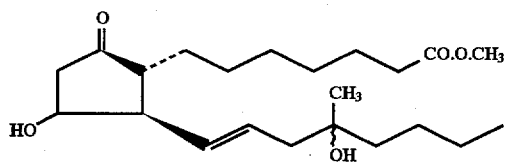

The synthetic method for preparing misoprostol and similar compounds disclosed in the aforementioned Pappo et.al. patent involves the preparation of a lower order lithium cuprate having unsaturated organic radicals associated with the copper ion, and the reaction of this lower order lithium cuprate with an appropriately chosen cyclopentenone, which in the case of misoprostol synthesis is methyl 7-(3RS)-tetrahydropyran-2-yloxy-5-oxocyclopent-1-ene)heptanoate. The lower order lithium cuprate used in this process, which in the case of misoprostol synthesis can be represented by the formula:

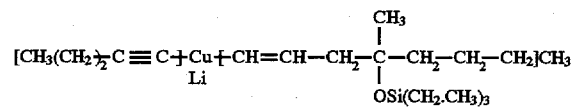

is made by a relatively complicated, multi-step process. The process involves reaction of an acetylenic alcohol with a trialkylsilyl halide to obtain the corresponding trialkylsilyl ether, addition of diisobutyl aluminum hydride across the acetylenic bond to produce the corresponding alkenyl aluminum derivative, reaction of this with iodine to obtain the silyl-protected 1-alkenyl iodide, and contact of this 1-alkenyl iodide with a lithium alkyl to form 1-alkenyl lithium which reacts with a cuprous acetylide to form the required lithium cuprate reagent.

Canadian patent 1,311,490 Campbell et.al. describes an improved and simplified process for preparing prostaglandins such as misoprostol, using higher order cuprates which will undergo conjugate addition to cyclopentenones. The higher order cuprates are prepared from vinyl stannane compounds, which are much easier to prepare than the vinyl iodides used in the Pappo et. al. patent process. These higher order cuprates are formed by reacting a higher order cuprate complex of formula:

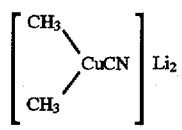

with a stannane of general formula $R_rSn.(R_2)_3$. The group $R_r$ from the stannane, which is a carbanion and is normally an unsaturated group corresponding to the side chain required in the final prostaglandin compound, exchanges with one of the methyl groups on the cuprate complex, presumably to form a mixed higher order cuprate of the formula:

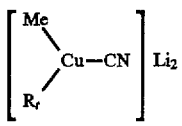

Alternative ligands to cyanide suggested in the Campbell et.al. patent are thiocyanate —SCN, sulfonyl-trifluoromethyl and thiophenyl, although only cyanide and thiocyanate are specifically exemplified.

It appears to be essential that the complex with vinyl group-containing ligands for reaction with enones such as cyclopentenones in prostaglandin synthesis be a copper complex. The straightforward reaction sequence to produce such a complex, where stannanes carrying the required vinyl group for addition onto the cyclopentenone nucleus are to be used, would be reaction of the appropriate vinyl stannane compound with an alkyl lithium such as n-butyl lithium to form a lithium vinyl species. This lithium vinyl compound could then be reacted with an organometallic copper compound, to exchange the vinyl group from the lithium compound with an organic radical from the copper compound, and hence produce the cuprate complex ready for reacting with the enone. However, the reaction of the alkyl lithium with the vinyl stannane will only take place at extremely low temperatures. The process disclosed in the Campbell et.al. patent overcomes this problem by first reacting the alkyl lithium with cuprous cyanide to obtain a first higher order complex, which is capable of reacting with the vinyl stannane at reasonable temperatures, to form a higher order cuprate capable of appropriate reaction with an enone.

The presence of ligands such as cyanide, with an empty π electronic orbital, on the cuprate complex has heretofore been believed to be necessary for the formation of higher order cuprate complexes with lithium alkyls (ref. 1). According to prior art teachings, copper halides such as iodides and bromides do not form higher order cuprates, making necessary the use of copper cyanide and the like as starting materials (ref. 1 & 2). This is unfortunate and undesirable, because of the highly toxic nature of copper cyanide. This renders it hazardous to handle, and severely complicates waste disposal problems of wash waters from a process which involves its use.

It is an object of the present invention to provide novel processes for making cuprate complexes capable of reacting with enone compounds.

It is a further object of the invention to provide such a process which avoids the use of toxic cyanide compounds.

SUMMARY OF THE INVENTION

According to the present invention, it has been discovered that organometallic cuprate complexes capable of reacting with enones to effect addition of an organic radical from the cuprate onto the enone, can be prepared by reaction of an alkyl lithium compound with a cuprous halide and reaction of the resulting complex with a vinyl stannane, provided that an excess amount of alkyl lithium is used initially and is present during the reaction to form the organometallic cuprate complex. Under such conditions, the vinyl group from the stannane successfully transfers to the cuprate, to form a complex which readily reacts with an enone e.g. a cyclopentenone to form a prostaglandin carrying the vinyl group originally in the stannane compound, as a substituent.

The process of the present invention thus not only adopts a new chemical approach, but also permits the use of simple and readily available starting materials, e.g. methyl lithium and a cuprous halide, and avoids the need for the highly toxic cuprous cyanide or the like. The reactions proceed smoothly at reasonable temperatures, to give good yields of intermediate and final products. Cuprous halides used in the process of the present invention copper (I) iodide, copper (I) bromide, copper chloride (I) and copper (I) fluoride, with the fluoride being the least preferred and the iodide and bromide being the most preferred.

The first stage in the process according to the invention is the reaction of the alkyl lithium (e.g. methyl lithium) with the cuprous halide. This requires a stoichiometry of two equivalents of methyl lithium and one equivalent of cuprous halide, to produce the lower order cuprate. The process of the invention, however, uses more than two equivalents of alkyl lithium, to provide a small excess of alkyl lithium in the reaction but not such a large excess as to promote excessive side reactions. However, if exactly two equivalents, or less than two equivalents, of alkyl lithium are used, little or no reaction is observed.

Thus according to one aspect of the present invention, there is provided a process for preparing an organometallic cuprate complex carrying an organic unsaturated ligand, said cuprate complex being capable of reaction with an enone to effect addition of the organic unsaturated ligand from the cuprate complex onto the enone, which comprises reacting in excess of two equivalents of lower alkyl lithium with one equivalent of a cuprous halide, and reacting the product thereof with a vinyl stannane compound of the general formula:

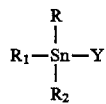

in which each of R, R$_1$, and R$_2$ is an independently selected lower alkyl radical and Y is an optionally substituted vinyl group.

DESCRIPTION OF THE PREFERRED EMBODIMENTS

The process of the invention is best further described and illustrated with reference to the use of methyl lithium and cuprous iodide as the starting materials, the preferred embodiments thereof. However, it is not to be construed as limited thereto. It will be readily apparent that other lower alkyl (C$_1$ to C$_6$) lithium compounds and other cuprous halides as outlined above can also be used.

The chemical mechanism by which the process of the present invention proceeds is not currently fully understood. The presence of excess alkyl lithium e.g. methyl lithium is essential for the successful operation of the process according to the invention. If only the stoichiometric amount (2 equivalents thereof) is used, no complex able to react with an enone is formed.

The extent of excess of the methyl lithium needs to be only small. The reaction proceeds satisfactorily if only a very small, catalytic amount of methyl lithium is present, over and above the stoichiometric two equivalents. Suitably at least about 2.05 equivalents of methyl lithium per equivalent of cuprous iodide. The upper limit of methyl lithium amount is dictated primarily by the need to minimize side reactions. It is preferred for practical reasons, for example, to continue with the reaction of the cuprate complex with the enone to prepare the prostaglandin, without removing from the reaction mixture the by-products and unreacted starting materials from the synthesis of the cuprate complex. If there is too much residual methyl lithium at this stage, 1,2-addition to the ketone (cyclopentenone) may occur, to produce unwanted by-products and reduce overall yield. Preferably, therefore, the amount of methyl lithium does not exceed about 4 equivalents per equivalent of cuprous halide, the most preferred range being from about 2.1:1 to about 2.25:1, and the optimum being about 2.2 equivalents.

The group Y, initially part of the stannane reactant, can be substantially any vinyl group-containing radical which is desired to be substituted onto a cyclopentenone nucleus to form a pharmaceutically active prostaglandin compound. This group Y in general corresponds to the formula:

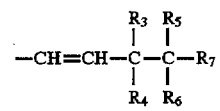

in which R$_3$, R$_4$, R$_5$, and R$_6$ are independently selected from hydrogen, C$_1$ to C$_6$ alkyl, C$_1$ to C$_6$ alkoxy, vinyl, hydroxy and protected hydroxy, and R$_7$ is C$_2$ to C$_4$ straight chain alkyl optionally interrupted by an ether linkage, or phenoxy. Preferred groups Y are those in which R$_7$ represents n-butyl and R$_5$ represents protected hydroxyl. Substantially any of the chemical groups conventionally used in organic synthetic chemistry to protect hydroxyl groups from chemical reaction, as set out in the standard literature, can be used as the hydroxyl protectant in the process of the present invention. Most preferred groups Y are those in which R$_7$ represents n-butyl, R$_3$ and R$_4$ represent hydrogen, R$_6$ represents methyl and R$_5$ represents protected hydroxyl, e.g. oxytrimethylsilyl protected hydroxyl.

The reaction of the excess methyl lithium with cuprous iodide suitably takes place in solution in an organic solvent, under strictly anhydrous conditions, since alkyl lithium compounds are extremely sensitive to water. The time of the reaction is suitably from about 5 minutes to two hours. The temperature of the reaction is suitably in the range −30° C.–10° C. Suitable solvents include tetrahydrofuran, dimethoxyethane, diethoxymethane, diethyl ether, diisopropyl ether, t-butylmethyl ether and the like.

The vinyl stannane compound, e.g. with R$_1$, R$_2$ and R being butyl, which is prepared separately, is added to the reaction mixture from the previous step. The conclusion of this reaction is signified by the presence of methyltributyl tin and the disappearance of the vinyl stannane compound and usually takes from about 5 minutes to about two hours. The order of addition of methyllithium or vinyl stannane compound is in general not critical and can be reversed. Methods of preparation of the appropriate vinyl stannane compounds are known, and form no part of the invention herein. In the case of misoprostol preparation using the process of the present invention, the vinyl stannane compound may have the formula:

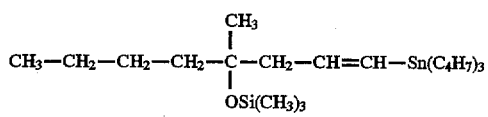

The vinyl stannane is added to the reaction mixture resulting from the reaction of the excess methyl lithium with cuprous iodide or bromide, without separating or isolating the reaction products and unreacted starting materials therefrom. The relative amounts of vinyl stannane and other reactants is relatively unimportant at this stage of the process, but is preferable about equimolar with the starting amount of cuprous iodide or bromide. The same organic solvent and generally the same reaction conditions as in the stage of reaction of the methyl lithium with the cuprous iodide or bromide can be used in this stage also. After the conclusion of the reaction of the vinyl stannane with the products of the earlier reaction, a process which normally takes about 5 minutes to two hours and the conclusion of which is indicated by the presence of methyltributyl tin and the disappearance of the vinyl stannane compound, the substituted cyclopentenone for formation of the prostaglandin can be added directly to the resulting reaction mixture, without the need to separate the resulting reaction products from the unreacted starting materials and by-products.

The preparation of the substituted cyclopentenone is also known procedure, and constitutes no part of the present invention. In the case of misoprostol preparation using the process of the present invention, the cyclopentenone may have the general formula, where Z is an appropriate protecting group:

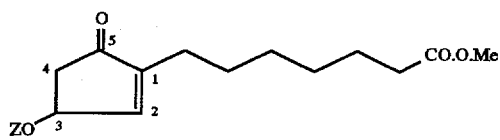

For preparation of other prostaglandin compounds by the process of the present invention (e.g. arbaprostil, gemeprost, trimoprostil, rioprostil, enprostil, enisoprost and viprostol), the substituent at position-1 of the cyclopenten-one ring will differ from that for preparation of misoprostol, e.g. in the presence of ethylenic unsaturation in the chain and/or in the identity of the end group. Such differences do not alter the course of the reaction of the cuprate complex made according to the invention, to any significant extent. In general, the group at the 1-position of the cyclopentenone can be represented as $R_8X$, where $R_8$ represents a $C_6$–$C_7$ straight-chain, saturated or unsaturated aliphatic hydrocarbon group, and X represents a carboxyl group, a lower alkyl esterified carboxyl group, a hydroxy group or a carbonyl-hydroxymethyl group. Similarly, other protectants may be used for the hydroxyl group at position-3.

The coupling reaction of the cuprate complex with the protected enone, which is in effect an addition reaction across the cyclopentene ring double bond, is effected by simply adding the protected enone to the reaction mixture in which the cuprate complex has been formed and is contained. The temperature of the reaction is suitably in the range from 0° C. to –80° C., preferably –50° C. to –80° C.

The crude, protected prostaglandin obtained can be deprotected and purified by standard methods to provide misoprostol.

The invention is further described, for illustrative purposes, with reference to the following specific examples.

DESCRIPTION OF THE SPECIFIC, MOST PREFERRED EMBODIMENTS

EXAMPLE 1

To a 1000 ml dried flask under a nitrogen atmosphere was added 74.6 g of (E)-trimethyl[[1-methyl-1-[3-(tributylstannyl)-2-propenyl]pentyl]oxy]silane, 125 ml anhydrous THF and 24.2 g of copper (I) iodide. The mixture was stirred at room temperature for 30 minutes and then it was cooled to –25° C. to –30° C. 98.8 ml of methyllithium (2.86M) in DEM was added dropwise and the resultant solution was stirred at –15° C. for 2 hours. Then the reaction mixture was cooled to –78° C. to –80° C. and 25 g of methyl 5-oxo-3-[(triethylsilyl)oxy]-1-cyclopentene-1-heptanoate in 100 ml of THF was added rapidly. After stirring the mixture for 5 minutes at –78° C., it was quenched into a mixture of 750 ml of aqueous ammonium chloride solution and 200 ml of ammonium hydroxide. The resulting mixture was warmed to room temperature and stirred until a deep blue aqueous layer was obtained. Ethyl acetate (2×250 ml) was used for extraction. Then the combined organic layers were washed with brine (2×150 ml) and subsequently dried over magnesium sulfate. After a filtration and concentration under reduced pressure, an oil (105 g) was obtained. This oil containing the protected prostaglandin was subjected to acidic deprotection (cat.PPTS, acetone and water) and purification (chromatography on silica gel) to provide 15.8 g (60%) of misoprostol. This product was identical ($^1$H NMR, $^{13}$C NMR and IR) to a standard sample of misoprostol.

EXAMPLE 2

To a 300 ml dried flask under a nitrogen atmosphere was added 4.45 g of copper (I) iodide and 60 ml of anhydrous THF. The mixture was cooled to 0° C. 35 ml of 1.4M methyllithium in diethyl ether was added dropwise and the resultant solution was stirred at 0° C. for 30 minutes. 13.7 g of (E)-trimethyl[[1-methyl-1-[3-(tributylstannyl)-2-propenyl]pentyl]oxy]silanein 5 ml of THF was added and then the mixture was stirred at 0° C. for 30 minutes. Then an additional 1.5 ml of 1.4M methyllithium in diethyl ether was added and the mixture was stirred at 0° C. for another 30 minutes. The reaction mixture was cooled to –78° C. and 10 g of methyl 5-oxo-3-[(triethyl-silyl)oxy]-1-cyclopentene-1-heptanoate in 10 ml of THF was added rapidly. After stirring the mixture for 5 minutes at –78° C., it was quenched into 210 ml of basic aqueous ammonium chloride solution. The resulting mixture was warmed to room temperature and stirred until a deep blue aqueous layer was obtained. Ethyl acetate (2×200 ml) was used for extraction. Then the combined organic layers were washed with water (10 ml), then with brine (25 ml) and subsequently dried over magnesium sulfate. After a filtration and concentration under reduced pressure, an oil (21 g) was obtained. This oil containing the protected prostaglandin was subjected to acidic deprotection (cat.PPTS, acetone and water) and purification (chromatography on silica gel) to provide 4.2 g (40%) misoprostol.

REFERENCES

1. "Organometallics in Synthesis: A Manual", Chapter 4, page 283–382; B. H. Lipshutz, Edited by M Schlosser, John Wiley & Sons, 1994.

2. B. H. Lipshutz, Synthesis, 325 (1987).

What is claimed is:

1. A process for preparing an organometallic cuprate complex carrying an organic unsaturated ligand, said cuprate complex being capable of reaction with an enone to effect addition of the organic unsaturated ligand from the cuprate complex onto the enone, which comprises reacting in excess of two equivalents of lower alkyl lithium with one equivalent of a cuprous halide, and reacting the product thereof with a vinyl stannane compound of the general formula:

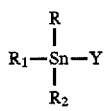

in which each of R, $R_1$, and $R_2$ is an independently selected lower alkyl group and Y is an optionally substituted vinyl group.

2. The process of claim 1 wherein from about 2.05 to about 4 equivalents of alkyl lithium is reacted with 1 equivalent of cuprous halide.

3. The process of claim 2 wherein the alkyl lithium compound is a $C_1$-$C_6$ straight chain alkyl lithium, and the cuprous halide is copper (I) iodide or copper(I) bromide.

4. The process of claim 3 wherein the alkyl lithium is methyl lithium.

5. The process of claim 3 wherein group Y in the vinyl stannane compound corresponds to the formula:

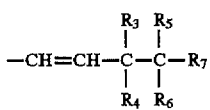

in which $R_3$, $R_4$, $R_5$, and $R_6$ are independently selected from hydrogen, $C_1$ to $C_6$ alkyl, $C_1$ to $C_6$ alkoxy, vinyl, hydroxy and protected hydroxy, and $R_7$ is $C_2$ to $C_4$ straight chain alkyl optionally interrupted by an ether linkage, or phenoxy.

6. The process of claim 5 in which $R_7$ represents n-butyl and $R_5$ represents protected hydroxyl.

7. The process of claim 5 wherein the molar ratio of alkyl lithium compound to copper (I) halide is from about 2.1:1 to about 2.25:1.

8. The process of claim 5 including the further, subsequent step of reacting the organometallic cuprate complex so formed with a 1-substituted, 3-substituted, cyclopent-1-en-5-one of the general formula:

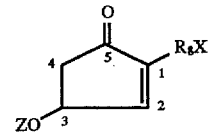

in which $R_8$ represents a $C_6$-$C_7$ straight-chain, saturated or unsaturated aliphatic hydrocarbon group, and X represents a carboxyl group, a lower alkyl esterified carboxyl group, a hydroxy group or a carbonyl-hydroxymethyl group; and Z represents hydrogen or a hydroxyl-protectant group; so as to effect 1,4-addition to the cyclopentenone and produce a synthetic prostaglandin with group Y at the 2-position of the cyclopentan-5-one nucleus.

9. The process of claim 8 wherein the substituted cyclopentenone compound is added to the reaction mixture resulting from the previous reaction step.

10. The process of claim 9 wherein the vinyl stannane reactant compound is (E)-trimethyl[[1-methyl-1-[3-(tributylstannyl)-2-propenyl]pentyl]oxy]silane, and the cyclopentenone compound is methyl 5-oxo-3-[(triethylsilyl)oxy]-1-cyclopentene-1-heptanoate, so as to prepare misoprostol as the final compound.

* * * * *